United States Patent [19]

Shasha et al.

[11] 4,039,586
[45] Aug. 2, 1977

[54] OXIDATION OF THIOLS TO DISULFIDES

[75] Inventors: Baruch S. Shasha, Peoria; William M. Doane, Morton; Edward I. Stout, Peoria, all of Ill.

[73] Assignee: The United States of America as represented by the Secretary of Agriculture, Washington, D.C.

[21] Appl. No.: 393,253

[22] Filed: Aug. 30, 1973

[51] Int. Cl.² .............................................. C07C 148/00
[52] U.S. Cl. ................................. 260/608; 260/534 S
[58] Field of Search ........................................ 260/608

[56] References Cited
U.S. PATENT DOCUMENTS

| | | | |
|---|---|---|---|
| 3,595,903 | 7/1971 | Greco | 260/608 |
| 3,647,481 | 3/1972 | Brodnitz | 260/608 |

*Primary Examiner*—Delbert R. Phillips
*Attorney, Agent, or Firm*—M. Howard Silverstein; David G. McConnell; Curtis P. Ribando

[57] ABSTRACT

A simple and selective technique for the oxidation of thiols resulted in high yields of the corresponding disulfides. The reaction is tailored so that all byproducts are either volatile or insoluble and the end product recovered easily in essentially pure form.

A nonexclusive, irrevocable, royalty-free license in the invention herein described, throughout the world for all purposes of the United States Government, with the power to grant sublicenses for such purposes, is hereby granted to the Government of the United States of America.

10 Claims, No Drawings

OXIDATION OF THIOLS TO DISULFIDES

BACKGROUND OF THE INVENTION

This invention relates to a method of oxidizing organic thiol compounds to disulfide compounds by the use of xanthides.

Thiols have been oxidized by biological oxidants such as flavins, cytochroms, and dehydroascorbic acid [G. E. Woodward, Biochem. J. 27: 1411 (1933)]; by inorganic chemicals such as iodine, hydrogen peroxide, potassium ferricyanide, and nitric acid (*Kirk-Othmer Encyclopedia of Chemical Technology*, Second Edition, Vol. 20, Interscience Publishers, New York, New York, 1969, pages 208-209); and by radiation using X-rays, $\beta$-rays, and $\gamma$-rays (P.C. Jocelyn, *Biochemistry of the SH Group*, Academic Press, 1972, page 102). However, most of these reagents are also capable of reacting with other oxidizable sites such as aldehyde and amino groups.

Thiols may also be oxidized by air, but considerable time is required and conditions vary for each thiol. Dimethyl sulfoxide has been used to convert thiols to disulfide, but this procedure requires heating the solution for 6-8 hr. at 60°-80° C. and the removal of byproducts and unreacted DMSO for isolation of the disulfide [C. N. Yiannios and J. V. Karabinos, J. Org. Chem. 28: 3246(1963)].

Organic sulfenyl chlorides have been reductively coupled to form symmetrical disulfides and sulfur-containing polymers [Kobayashi et al., J. Polym. Sci. 10: 3317-3327 (1972)].

We have found a new method for preparing disulfide compounds which comprises reacting a xanthide with an organic thiol, at least one of which is in solution in a suitable solvent, in the presence of an amount of tertiary amine sufficient to initiate the reaction, xanthide and organic thiol being present in a 1:2 molar ratio, respectively.

This method has the advantage of being easy, quick, and general. The reaction is easily taylored so that the byproducts are either volatile or insoluble. Thus, recovery of the essentially pure disulfide compound is simply a matter of filtration or drying. When the reaction utilizes insoluble xanthides in a bed or column, the method becomes a continuous process. Organic disulfide products are used in a variety of ways. Tetramethyl- and tetraethylthiuran disulfides and dimorpholine disulfide aid in the vulcanization of rubber. Cellulose disulfides, such as in cotton fibers which are crosslinked, give crease resistance to the material, However, aside from product use, the method itself is useful. Since the reaction is quantitative and applicable to essentially all thiol compounds, the method is useful in the analytical determination of thiols. Iodine oxidation is the usual analytical procedure for this determination, but iodine is reactive with many other functional groups including multiple bonds. The method can also be used in the petroleum industry where petroleum is "sweetened" by the oxidation of thiol to disulfide.

DETAILED DESCRIPTION OF THE INVENTION

The preparation of unsymmetrical disulfides have been reported by Brois et al. [J. Amer. Chem. Soc. 92: 7629 (1970)]who induced the fragmentation of sulfenyl thiocarbonates with thiol compounds. Kobayashi et al. [Polym. Lett. Ed. 11: 225-228 (1973)]discloses the preparation of disulfide polymers from bis(oxycarbonyl) disulfides and dithiols.

Xanthide [i.e., dithiobis(thioformate) derivatives of organic compounds]starting materials of the invention include xanthides prepared by oxidative coupling xanthate derivatives of any organic compound capable of forming a xanthate derivative. Compounds of this type include alkyl alcohols ranging from methanol to fatty acid alcohols, starch, and cellulose, and compounds having other oxygen-, halogen-, nitrogen-, or sulfur-containing substituents.

The invention is also adaptable to essentially any organic thiol-containing compound including straight-chain, branched-chain, and cyclic alkyl thiols and substituted alkyl thiols such as methane thiols, dodecane thiols, isopropyl thiols, hexane thiols, amino acids, thioglycolic acids, hydroxy alkyl thiols, and fatty acid thiols; aryl and substituted aryl thiols such as benzyl thiol and phenyl thiol, p-chlorobenzene thiol and p-hydroxylbenzene thiol; alkyl dithiols such as 1,2-ethanedithiol and 1,4-butanedithiol; and polythiols such as thiol starch, thiol cellulose, protein (wool, enzymes), and polyvinyl thiol.

The preferred tertiary amines used in accordance with the invention include pyridine and triethylamine. However, with certain starting materials, inorganic bases such as sodium hydroxide can be used. The tertiary amines seem to act as catalysts and are needed only in amounts sufficient to initiate the reaction. Tertiary amines can also be suitable solvents for the reactants and are in these instances used in great excess of their reaction-initiating quantities.

Suitable solvents are those that will dissolve at least one of the reactants and will not interfere with the reaction (i.e., react with or prevent the reaction of either reactant). Preferably the solvent should also be sufficiently volatile to insure easy removal. Such solvents include water, pyridine, benzene, acetone, diethyl ether, methanol, and ethanol.

For the reaction to proceed quickly, only one of the two reactants need be in solution. In fact, in certain utilities, it is desirable to have one of the reactants insoluble in the solvent. Insoluble xanthides such as starch, crosslinked starch, and cellulose xanthides when placed in a bed or column react according to the invention with thiols in solutions which are percolated through the bed or column. In this manner a continuous feed of thiol solution results in a continuous elution of disulfide from the xanthide column. It is necessary to periodically regenerate the xanthide in the column by percolating a solution of alkali and carbon disulfide through the bed followed by a solution of sodium nitrite. Since carbon disulfide is given off by the xanthide-thiol reaction, it can be collected and used in the rexanthation process. The continuous process is possible because the reaction is almost instantaneous when the reactants come together at room temperatures (i.e., 25°-30° C.) in the presence of a tertiary amine.

Since the reaction is quantitative (i.e., xanthides and thiols react in a 1:2 molar ratio, respectively) and essentially instantaneous, it lends itself to an analytical procedure for determination of thiol groups. It is preferable to use a low molecular weight xanthide such as methyl xanthide, especially when analyzing a high molecular weight thiol such as starch or cellulose thiol.

The following examples are intended to further illustrate the invention and should not be construed as limiting the scope of the invention as defined by the claims.

PREPARATION OF XANTHIDE

Methyl xanthide [dimethyl dithiobis(thioformate)]: 25 g. of methanol were added to a solution of 30 g. of potassium hydroxide in 30 ml. of water. The mixture was cooled to 5° and treated with 30 ml. carbon disulfide. After stirring for 10 min., 25 g. of sodium nitrite was added. Then the pH was adjusted to about 3 with 30 percent acetic acid. The xanthide thus formed was extracted with ether. Evaporation of the ether gave 37 g. of methyl xanthide.

Starch xanthide containing 23 percent sulfur (0.8 degree of substitution) was prepared in the same manner.

EXAMPLE 1

To a solution of 1.4 g. of p-chlorobenzenethiol in 5 ml. pyridine, 960 mg. of methyl xanthide was added in one portion. Evaporation of excess pyridine and volatile byproduct gave the known bis(p-chlorophenyl) disulfide in quantitative yield (1.4 g.). No free thiol could be detected by titration with iodine. The product was easily recrystallized from ethanol. Similar results were obtained using ethyl instead of methyl xanthide.

EXAMPLE 2

A solution of 1.4 g. of p-chlorobenzenethiol in 9 ml. of pyridine was treated with 3 g. of starch xanthide containing 23 percent sulfur. After standing for 10 min., 15 ml. of acetone was added and the mixture was filtered. Evaporation of excess solvents gave 1355 mg. of bis(p-chlorophenyl) disulfide.

EXAMPLE 3

A solution of 2 g. of benzenethiol in 2 ml. of pyridine was treated with 2 g. of methyl xanthide. Evaporation of solvents gave the phenyl disulfide in quantitative yield. The reaction was somewhat slower when the experiment was repeated under similar conditions but using only 100 mg. of pyridine.

EXAMPLE 4

One gram of benzenethiol was mixed with 1 g. of methyl xanthide and treated with 70-mg. of triethylamine. On standing for a few minutes, the phenyl disulfide crystallized out quantitively. Similar results were obtained when the triethylamine was replaced with 50 mg. 5N sodium hydroxide.

EXAMPLE 5

One gram of 3-mercaptopropionic acid in 5 ml. of pyridine was mixed with 1 g. methyl xanthide. Evaporation of excess solvent gave the known propionic acid disulfide in quantitative yield. The product was easily recrystallized from water.

EXAMPLE 6

A solution of 1.2 g. of 4-mercaptophenol in 5 ml. pyridine was treated with 1 g. of methyl xanthide. In evaporation of solvents the corresponding known phenol disulfide (1.1 g.) was obtained which was crystallized from a mixture of ligroin-benzene.

EXAMPLE 7

A solution of 350 mg. of cysteine in o.5 ml. of water was mixed with 214 mg. of methyl xanthide and 0.5 ml. of pyridine. The corresponding disulfide, cystine, precipitated almost immediately from the solution. After dilution with 10 ml. of water, the mixture was filtered and cystine was dried to yield 200 mg.

EXAMPLE 8

A solution of 1.55 g. of ethane dithiol was mixed with 3.52 g. methyl xanthide and 3 ml. of pyridine. Evaporation of the pyridine gave 1.2 g. of acetone insoluble polymeric disulfide with m.p. 130°–150°.

EXAMPLE 9

To a solution of cysteine hydrochloride (1.75 g.) in ethanol (5.0 ml.) were added methyl xanthide (1.07 g.) and pyridine (0.5 g.). Immediately, a white precipitate formed. The mixture was stirred for 1 min., kept for 5 min., and filtered. The solid was washed with ethanol (10 ml.) and acetone (10 ml.) and dried. Yield of cystine was 1.09 g., 89 percent, m.p. decomposed 260°; S, 26.5 percent (theory, 26.7 percent).

We claim:

1. A method of preparing disulfide compounds by the oxidative coupling of organic thiols which comprises reacting a xanthide with an organic thiol, at least one of which is in solution in a suitable solvent, in the presence of an amount of a tertiary amine sufficient to initiate to reaction, said xanthide and organic thiol being present in a 1:2 molar ratio, respectively.

2. A method of preparing disulfide compounds as defined in claim 1 wherein the xanthide is an alkyl xanthide having from about 4 to 40 carbons.

3. A method of preparing disulfide compounds as defined in claim 1 wherein the xanthide is a polysaccharide xanthide.

4. A method of preparing disulfide compounds as defined in claim 1 wherein the organic thiol is selected from the group consisting of alkyl thiols and substituted alkyl thiols containing from 1 to 20 carbon atoms and from one to two thiol groups.

5. A method of preparing disulfide compounds as defined in claim 1 wherein the organic thiol is selected from the group consisting of benzyl and substituted benzyl thiols, phenyl and substituted phenyl thiols.

6. A method of preparing disulfide compounds as defined in claim 1 wherein the organic thiol is a polythiol compound.

7. a method of preparing disulfide compounds as defined in claim 3 wherein the polysaccharide xanthide is starch xanthide.

8. A method of preparing disulfide compounds as defined in claim 6 wherein the polythiol compound is a thiol-containing protein.

9. a method of preparing disulfide compounds as defined in claim 6 wherein the polythiol compound is a polysaccharide thiol.

10. A method of preparing disulfide compounds as defined in claim 9 wherein the polysaccharide thiol is selected from the group consisting of starch thiol and cellulose thiol.

* * * * *